US012805948B2

(12) United States Patent
Dunki-Jacobs et al.

(10) Patent No.: US 12,805,948 B2
(45) Date of Patent: Nov. 24, 2026

(54) DONGLE AND CONTROL INTERFACE FOR CONTROL OF A LAPAROSCOPIC DEVICE

(71) Applicant: Standard Bariatrics, Inc., Cincinnati, OH (US)

(72) Inventors: Adam R. Dunki-Jacobs, Cincinnati, OH (US); Jonathan R. Thompson, Cincinnati, OH (US)

(73) Assignee: STANDARD BARIATRICS, INC., Cincinnati, OH (US)

( * ) Notice: Subject to any disclaimer, the term of this patent is extended or adjusted under 35 U.S.C. 154(b) by 71 days.

(21) Appl. No.: 18/623,221

(22) Filed: Apr. 1, 2024

(65) Prior Publication Data

US 2024/0325096 A1 Oct. 3, 2024

Related U.S. Application Data

(60) Provisional application No. 63/455,795, filed on Mar. 30, 2023.

(51) Int. Cl.
*A61B 34/30* (2016.01)
*A61B 17/00* (2006.01)
*A61B 17/068* (2006.01)

(52) U.S. Cl.
CPC ............ *A61B 34/30* (2016.02); *A61B 17/068* (2013.01); *A61B 2017/00115* (2013.01); *A61B 2017/00199* (2013.01); *A61B 2017/00973* (2013.01); *A61B 2034/302* (2016.02)

(58) Field of Classification Search
CPC ....... A61B 34/30; A61B 34/37; A61B 17/068; A61B 17/07207; A61B 2017/00115; A61B 2017/00199; A61B 2017/00973; A61B 2017/00017; A61B 2017/00128; A61B 2017/00212; A61B 2017/00221; A61B 2017/00398; A61B 2017/00477; A61B 2034/302
USPC .................. 700/245; 701/436; 606/130, 128; 345/420, 424, 419; 703/11; 83/768
See application file for complete search history.

(56) References Cited

U.S. PATENT DOCUMENTS

| | | | | |
|---|---|---|---|---|
| 5,788,688 | A * | 8/1998 | Bauer | A61B 90/36 |
| 9,554,866 | B2 * | 1/2017 | Cunningham | A61B 18/14 |
| 9,936,953 | B2 | 4/2018 | Thompson et al. | |
| 10,912,562 | B2 | 2/2021 | Dunki-Jacobs et al. | |
| 2003/0050733 | A1 | 3/2003 | Wang et al. | |
| 2010/0228264 | A1 | 9/2010 | Robinson et al. | |
| 2010/0274087 | A1 * | 10/2010 | Diolaiti | A61B 34/71 |
| 2016/0000301 | A1 * | 1/2016 | Langell | A61B 1/00105 |
| 2017/0189096 | A1 | 7/2017 | Danziger et al. | |

(Continued)

FOREIGN PATENT DOCUMENTS

JP 6914942 B2 8/2021

*Primary Examiner* — Ellis B. Ramirez
(74) *Attorney, Agent, or Firm* — BakerHostetler

(57) ABSTRACT

Systems, methods, and devices for use with a computerized surgical manipulation system, comprising a control interface communicatively coupled to a laparoscopic device detached from a robot of the computerized surgical manipulation system, wherein the control interface is positioned at a location physically remote from the laparoscopic device; and a dongle communicatively coupled to the control interface and the laparoscopic device, wherein the dongle is configured to enable operation of the laparoscopic device from the control interface and directly from the laparoscopic device.

20 Claims, 14 Drawing Sheets

(56) References Cited

U.S. PATENT DOCUMENTS

| | | | | |
|---|---|---|---|---|
| 2019/0038371 | A1* | 2/2019 | Wixey | A61B 34/00 |
| 2019/0201136 | A1* | 7/2019 | Shelton, IV | G16H 40/63 |
| 2020/0100830 | A1* | 4/2020 | Henderson | H04L 67/10 |
| 2021/0322017 | A1* | 10/2021 | Shelton, IV | A61B 1/0661 |

* cited by examiner

DONGLE AND CONTROL INTERFACE FOR CONTROL OF A LAPAROSCOPIC DEVICE

CROSS-REFERENCE TO RELATED APPLICATIONS

This patent application claims the benefit of U.S. Provisional Patent Application Ser. No. 63/455,795 filed on Mar. 30, 2023 and entitled "Dongle And Control Interface For Control Of A Laparoscopic Device", the disclosure of which is hereby incorporated by reference herein in its entirety and made part of the present U.S. utility patent application for all purposes.

BACKGROUND

The disclosed technology relates in general to robotic-assisted surgical technology and more specifically to systems, devices, and methods for controlling and firing surgical staplers used for laparoscopic surgery from a remote location through a dongle and control interface.

Robotic surgery, also called robot-assisted surgery, allows doctors to perform many types of complex procedures with more precision, flexibility, and control than is possible with conventional techniques. Robotic surgery is usually associated with minimally invasive surgery, or procedures performed through small incisions. However, it is also sometimes used in certain traditional open surgical procedures.

Example clinical robotic surgical systems typically include a camera arm and multiple mechanical or robotic arms with surgical instruments attached thereto. The surgeon can control the arms while at a surgical console near the operating table or bedside through one or more control interfaces. The console gives the surgeon a high-definition, magnified, three-dimensional view of the surgical site, without the need for the surgeon to scrub in.

Robotic surgical systems can be utilized to assist in laparoscopic procedures wherein a stapling device is ultimately utilized to staple an anatomical structure of a patient. In such laparoscopic procedures, the stapling device is undocked from the mechanical or robotic arms of the robotic surgical system, and a nurse or other operating room staff member must: (i) hold or support the stapling device in place; (ii) correctly align and position the device on/around the desired anatomical structure; and (iii) actuate or fire the device to apply the staples, all while the surgeon remains at the surgical console. However, most surgeons are uncomfortable with nurses or operating room staff members placing and firing the stapling device bedside for a variety of reasons, including liability and the high-level of precision and accuracy required during laparoscopic surgeries. In such robot-assisted surgeries, surgeons must remove themselves from the console, scrub in and operate the stapling device while positioned within the patient, thereby diminishing surgical efficiency. Accordingly, there is an ongoing need for systems, devices, and methods that permit doctors and qualified individuals to control and fire surgical staplers from the remote console of the robotic surgical system.

SUMMARY

The following provides a summary of certain example implementations of the disclosed technology. This summary is not an extensive overview and is not intended to identify key or critical aspects or elements of the disclosed technology or to delineate its scope. However, it is to be understood that the use of indefinite articles in the language used to describe and claim the disclosed technology is not intended in any way to limit the described technology. Rather the use of "a" or "an" should be interpreted to mean "at least one" or "one or more".

One implementation of the disclosed technology provides a surgical control system for use with a computerized surgical manipulation system, comprising a control interface communicatively coupled to a laparoscopic device detached from a robot of the computerized surgical manipulation system, wherein the control interface is positioned at a location physically remote from the laparoscopic device; and a dongle communicatively coupled to the control interface and the laparoscopic device, wherein the dongle is configured to enable operation of the laparoscopic device from the control interface and directly from the laparoscopic device.

In some implementations of the surgical control system, wherein the control interface or the dongle includes an override feature that, when activated, disables direct operation from the laparoscopic device, but maintains operation of the laparoscopic device from the control interface. In various implementations, the laparoscopic device is a surgical stapler configured to staple an anatomical structure of a patient during a minimally invasive procedure, the surgical stapler comprising an end effector having a clamping mechanism with an anvil assembly and a cartridge assembly; and an operating system comprising a trigger having an up-switch and a down-switch, wherein activation of the up-switch opens the clamping mechanism, and wherein activation of the down-switch closes the clamping mechanism. In some implementations, the control interface is a foot-operable device comprising a plurality of input controls, wherein each of the input controls, when activated, communicate with the operating system of the surgical stapler to perform an action. In some implementations, activation of a first input control opens the clamping mechanism of the end effector; activation of a second input control closes the clamping mechanism of the end effector; first activation of a third input control initiates a timeout period before the surgical stapler cuts and staples the anatomical structure of the patient; and second activation of the third input control causes the surgical stapler to enter a firing mode. The timeout period may include an alert configured to indicate a start of the timeout period, an end of the timeout period, remaining time of the timeout period, or combinations thereof, wherein the alert may be a visual indicator, an audio indicator, or combinations thereof. In some implementations, the timeout period lasts 15 second. Some implementations of the input controls include buttons, switches, pedals, or combination thereof. In some implementations, the foot-operable device is integrated into a surgical console of the computerized surgical manipulation system. In some implementations, the control interface is a hand-operable device positioned on an exterior of a surgeon console of the computerized surgical manipulation system, the hand-operable device comprising a plurality of input controls, wherein each of the input controls, when activated, communicate with the operating system of the surgical stapler to perform an action, wherein the plurality of input controls may include buttons or switches which, when activated, open the clamping mechanism, close the clamping mechanism, enter a firing mode, or combinations thereof. In some implementations, the hand-operable device is a hand control that can move with one or more degrees of freedom. In various implementations, the hand-operable device is a control panel. In some implementations, the control interface is an audio recognition device having a microcontroller configured to receive audio content from an audio capture device during the minimally invasive procedure, wherein the audio content is one or more instructions from a user; analyze the audio content to determine a meaning for the one or more instructions; and provide a command to the surgical stapler to perform one or more actions based on the meaning of the one or more instructions. In various implementations, the one or more actions include opening the clamping mechanism, closing the clamping mechanism, entering a firing mode, or combinations thereof. In some implementations, the detached laparoscopic device is supported by a trained individual positioned bedside to a patient. The dongle is incorporated into the laparoscopic device in various implementations.

Another implementation of the disclosed technology provides a surgical control system for use with a computerized surgical manipulation system. The surgical control system comprises a surgical stapler configured to staple an anatomical structure of a patient during a minimally invasive procedure, the surgical stapler including an end effector having a clamping mechanism with an anvil assembly and a cartridge assembly; and an operating system comprising a trigger having an up-switch and a down-switch, wherein activating the up-switch opens the clamping mechanism, and wherein activating the down-switch closes the clamping mechanism; a control interface communicatively coupled to stapling device, wherein the control interface is positioned at the computerized surgical manipulation system physically remote from the stapling device; and a dongle communicatively coupled to the control interface and the stapling device, wherein the dongle is configured to enable operation of the stapling device from the control interface and directly from the stapling device, wherein the control interface or the dongle includes an override feature that, when activated, disables direct operation from the surgical device, but maintains operation of the surgical device from the control interface, and wherein the surgical stapler is separate from the computerized surgical manipulation system and supported by a trained individual positioned bedside to the patient.

In some implementations, the control interface is a foot-operable device comprising a plurality of input controls, wherein each of the input controls, when activated, communicate with the operating system of the surgical stapler to perform an action. In some implementations, the control interface is a hand-operable device positioned on an exterior of a surgeon console of the computerized surgical manipulation system, the hand-operable device comprising a plurality of input controls, wherein each of the input controls, when activated, communicate with the operating system of the surgical stapler to perform an action. In some implementations, the control interface is an audio recognition device having a microcontroller configured to receive audio content from an audio capture device during the minimally invasive procedure, wherein the audio content is one or more instructions from a user; analyze the audio content to determine a meaning for the one or more instructions; and provide a command to the surgical stapler to perform one or more actions based on the meaning of the one or more instructions.

It should be appreciated that all combinations of the foregoing concepts and additional concepts discussed in greater detail below (provided such concepts are not mutually inconsistent) are contemplated as being part of the technology disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the descriptions provided herein are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein:

FIGS. 12A-12B depict additional exemplary control interfaces for use with the surgical control system of FIG. 4, wherein FIG. 12A depicts the control interface as a hand control, and wherein FIG. 12B depicts the control interface as a hand-operated control panel;

DETAILED DESCRIPTION

Figure 1:
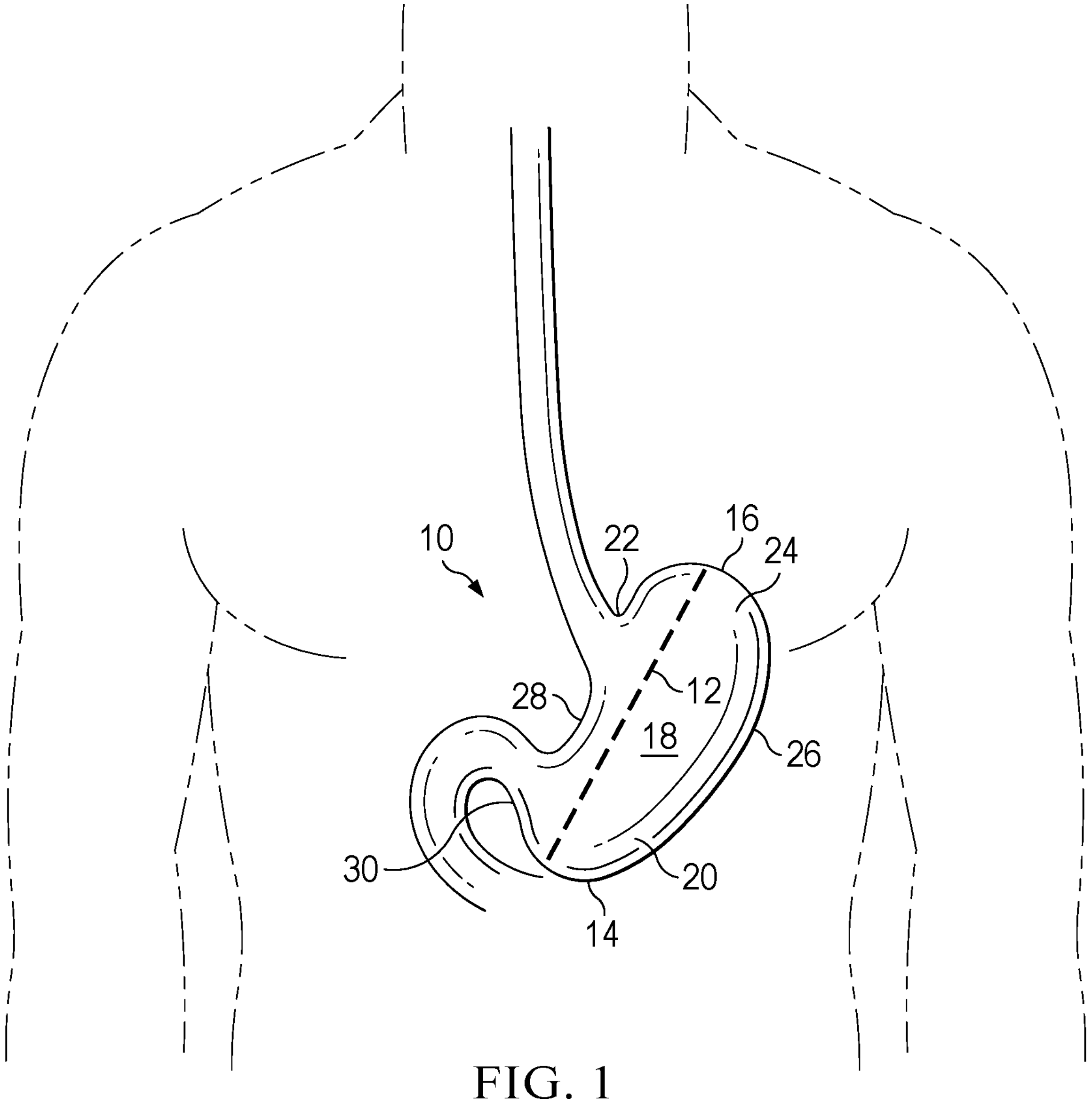
FIG. 1 depicts the anatomy of a stomach.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed technology. Accordingly, the following implementations are set forth without any loss of generality to, and without imposing limitations upon, the claimed subject matter.

The examples discussed herein are examples only and are provided to assist in the explanation of the apparatuses, devices, systems, and methods described herein. None of the features or components shown in the drawings or discussed below should be taken as required for any specific implementation of any of these the apparatuses, devices, systems or methods unless specifically designated as such. For ease of reading and clarity, certain components, modules, or methods may be described solely in connection with a specific Figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example implementations described herein can be used, for example, in a sleeve gastrectomy procedure or resection of the stomach utilizing a computerized surgical manipulation system, or also referred to as a robotic surgical system. It will be appreciated, however, that the disclosed systems, devices, and methods may be used in other procedures involving other anatomical structures, for example, in a parenchymal resection, lung volume reduction surgery, or other procedures involving the lung. Further, embodiments described herein may be useful in an anatomic resection, such as, a lobectomy, a non-anatomic parenchymal resection, or other procedures involving the liver, or in a partial nephrectomy, total nephrectomy, or other procedures involving the kidney.

Laparoscopic and surgical stapling device compatible with the disclosed technology are described in U.S. Pat. Nos. 9,936,953 and 10,912,562, which are incorporated by reference herein in their entireties, for all purposes. Some implementations of the stapling devices disclosed in U.S. Pat. Nos. 9,936,953 and 10,912,562 include end effectors for use by a surgeon to staple an anatomical structure of a patient during minimally invasive procedures. As shown in the Figures of U.S. Pat. No. 9,936,953, example end effectors include an anvil having a first end, a second end, and a face that is positionable on the first side of the anatomical structure; a cartridge configured to house a plurality of staples and that includes a first end, a second end, and a face that is positionable on the second side of the anatomical structure; and a flexible member that movably couples the first end of the anvil to the first end of the cartridge, wherein the anvil and the cartridge slidably receive the flexible member, and wherein the second end of the anvil is movably coupled to the second end of the cartridge. As shown in the Figures of U.S. Pat. No. 10,912,562, example end effectors include an upper jaw connected to a lower jaw by a simple hinge at the distal end of the stapler and by a master link or rigid link at the proximal end of the stapler. The upper jaw may include an anvil assembly that further includes an anvil frame, an anvil plate, and an anvil plate channel formed therein. The lower jaw may include a cartridge assembly that further includes a cartridge frame, a cartridge plate with a cartridge plate channel formed therein, and a cartridge for containing surgical staples.

Example implementations of the disclosed systems, methods, and devices provide a dongle and control interface assembly for use with a robotic surgical system that permits doctors and qualified individuals to control and operate a surgical stapling device, and to clamp, resect, and staple an organ or other tissue, from a remote location at a surgical console. As discussed herein, the disclosed systems, methods, and devices advantageously enables control of the stapling device at two points: (1) by a nurse or other operating room staff member physically holding or supporting the stapling device at the patient's side (i.e. bedside); and/or (2) by the doctor/surgeon at the remote surgical console. These points of control allow for increase efficiency of laparoscopic surgeries by, for example, minimizing the need of surgeons to physically control and actuate the stapling device bedside; and reducing the need for surgeons to undock a mechanical or robotic arm on the robotic surgical system to control the stapling device, thereby enabling control of at least three devices at one time.

Surgical instruments in accordance with the example implementations disclosed herein can be used in conjunction with the robotic surgical system. In some example implementations, the robotic surgical system can include a surgical/surgeon's console, a patient cart, a vision cart, and other mobile carts, wherein the vision cart can include a camera system, and the patient cart and mobile cart can include one or more robotic arms with supports that can each selectively receive various surgical instruments. The arms of some robotic surgical system have a series of joints to allow for a full range of movement of the arms during surgery. Example camera systems can include, for example, a dual lens optical system representing the left and right eyes. The spatial separation of these images can be projected to the surgeon's eyes in the binocular viewer to allow for true 3-D image perception at the console. Various instruments, such as the surgical instruments in accordance with the present disclosure, can be coupled to the various arms and are easily and rapidly changeable by the nurse or other operating room staff member at the patient side.

FIG. 1 depicts the anatomy of stomach 10 and example resection line 12 for a vertical sleeve gastrectomy. Stomach 10 generally includes inferior end 14, superior end 16, anterior side 18, and posterior side 20. Gastroesophageal junction 22 opens into stomach 10 and is a common landmark in bariatric surgeries. Fundus 24 and the section of stomach 10 defined by greater curvature 26 are generally the parts of stomach 10 removed during a vertical sleeve gastrectomy. The remaining pouch or sleeve may be generally defined by lesser curvature 28 and resection line 12, which presents a stomach with a significantly reduced volume. The desired location of resection line 12 may be about 0.5 cm to about 2 cm away from gastroesophageal junction 22 and about 2 cm to about 10 cm away from pylorus 30. In accordance with implementations, the systems, devices, and methods discussed herein may be utilized to form high quality, consistent resection lines during a vertical sleeve gastrectomy by a surgeon or qualified individual that is remote from the surgical stapling device.

Figure 2:
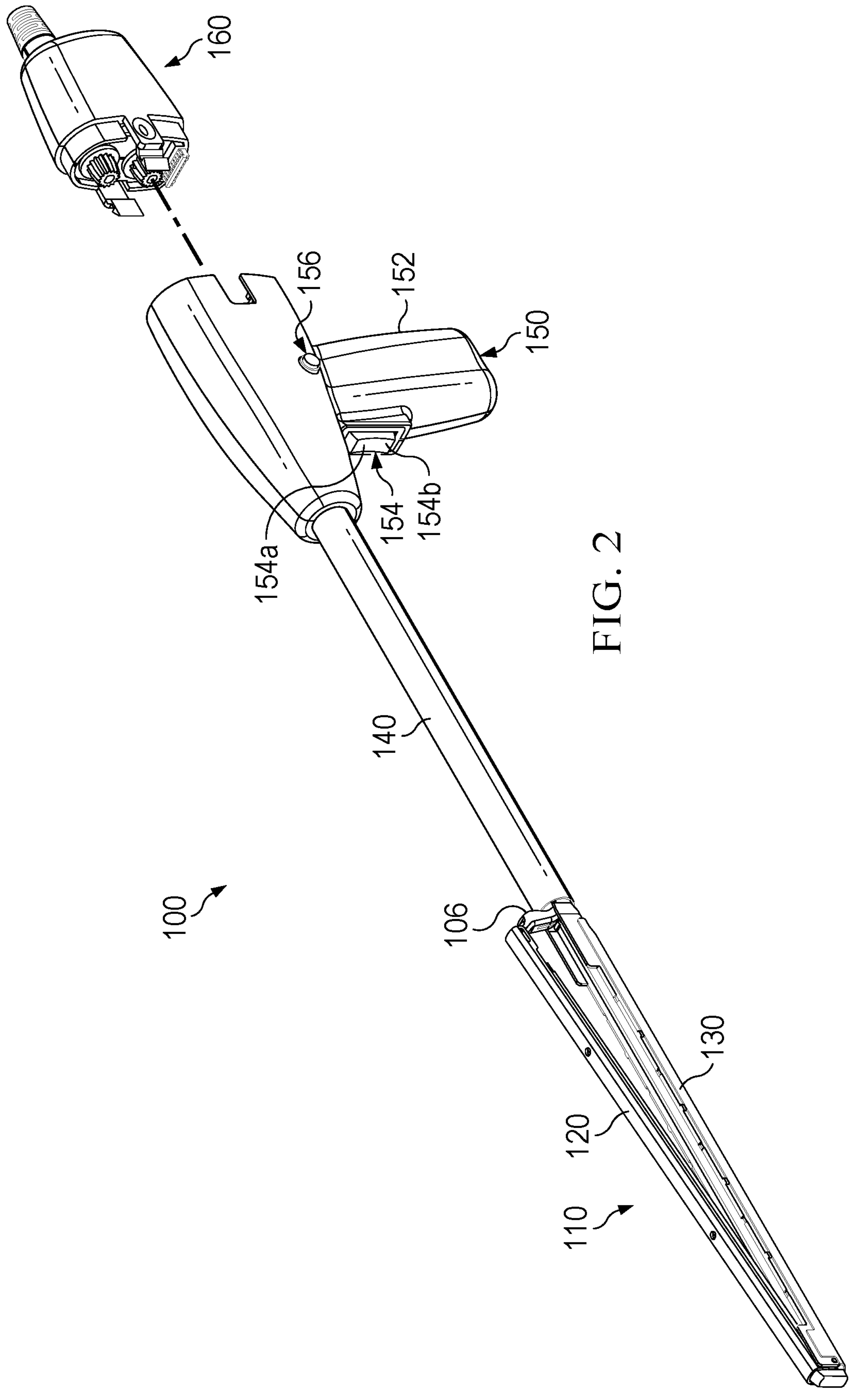
FIG. 2 depicts a perspective view of a surgical stapling device having an end effector, in accordance with an example implementation of the present disclosure.

FIG. 2 is a perspective view of an exemplary surgical stapling device 100 having an end effector 110, which includes an anvil assembly 120 that functions as a first jaw, a cartridge assembly 130 that functions as a second jaw, and a master link 106. Surgical stapling device 100 further includes a support tube 140, a handle portion 150, and a motor assembly 160. End effector 110 is connected to handle portion 150 via support tube 140. Handle portion 150 includes a handle 152 and a trigger 154 having an up switch 154*a* and a down switch 154*b* for actuating the stapling device 100.

Still referring to FIG. 2, handle portion 150 further includes a mode button 156 for switching between operational modes. For example, in a first mode, trigger 154 can be pressed upwards via up switch 154*a* to open the jaws or pressed downward via down switch 154*b* to close the jaws. When the jaws are in a closed position, mode button 156 can be depressed to transition the stapling device 100 into a firing mode. When in the firing mode, depressing trigger 154 can fire the stapling device 100 to simultaneously form a staple line comprising of one or a plurality of rows of staples while cutting tissue. In one embodiment, depressing trigger 154 in the firing mode can deploy a staple line including, for example, six rows of staples, where a knife (not shown) can simultaneously cut tissue between a third and a forth row of the staples.

Figure 3:
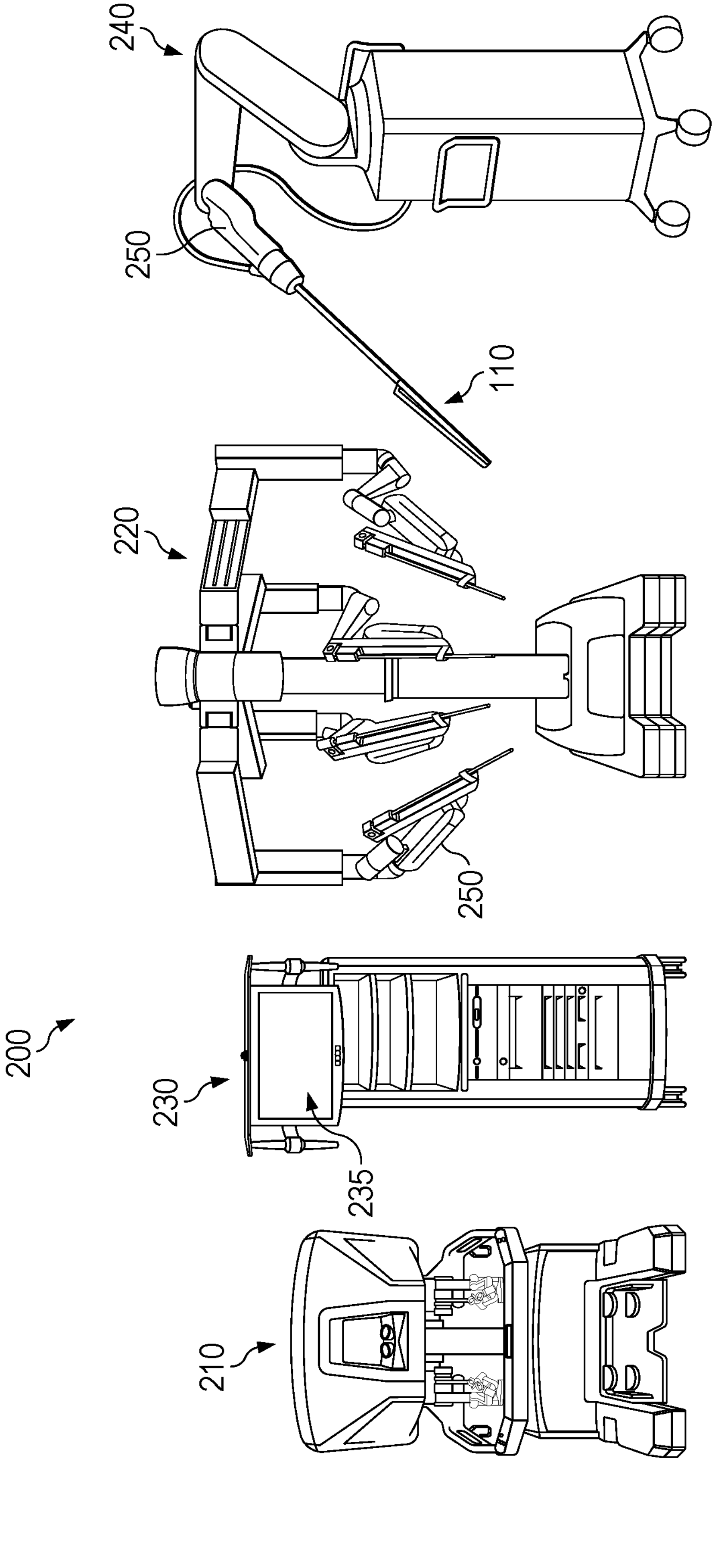
FIG. 3 depicts a robotic surgical system including a surgical console, a vision cart, a patient cart having a plurality of arms, and a mobile cart having a single, independent arm, in accordance with an example implementation of the present disclosure.

FIG. 3 depicts an example robotic surgical system 200 comprising a surgical/surgeon's console 210, a patient cart 220, a vision cart 230, and mobile carts 240, wherein vision cart 230 can include a camera system 235, and patient cart 220 and mobile cart 240 can include one or more robotic arms 250. Mobile cart 240 supporting surgical device 100 may be positioned at the patient's side instead of the nurse or other operating room staff member having to physically hold surgical device 100.

Figure 4:
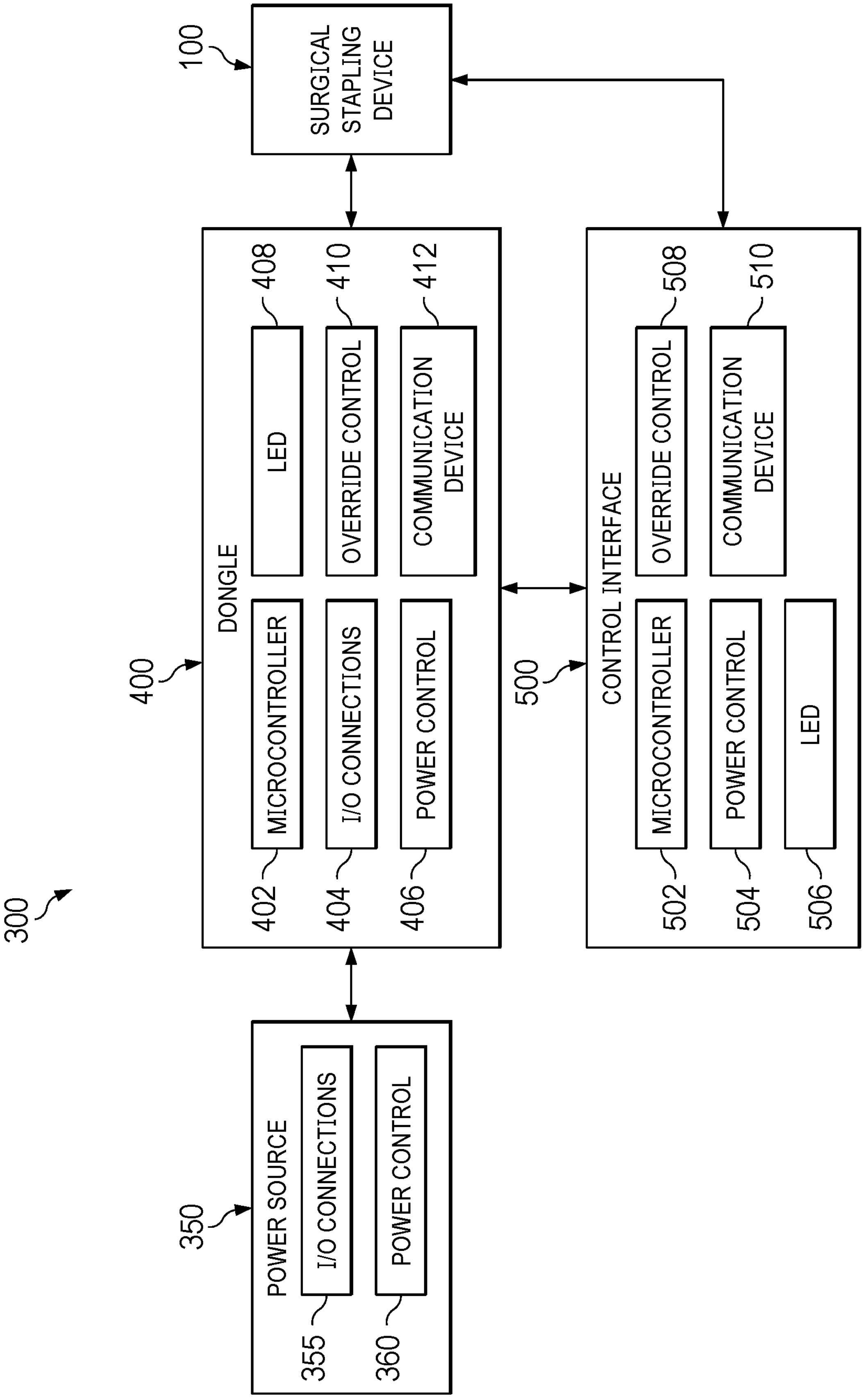
FIG. 4 is a block diagram of an example implementation of a surgical control system for use with the robotic surgical system of FIG. 3, wherein the surgical control system comprises a control interface, a dongle, the surgical stapling device of FIG. 2, and a power source.

FIG. 4 depicts a block diagram of an example implementation of a surgical control system 300 for use with robotic surgical system 200. Example surgical control system 300 includes the following components that, when used together, allow an individual to selectively control and fire surgical stapling device 100 from surgeon's console 210 that is remote from surgical stapling device 100 and/or control and fire surgical stapling device 100 bedside. Example surgical control system 300 includes surgical stapling device 100, a power source 350, a dongle 400, and a control interface 500.

Power source 350 includes a set of I/O connections 355 and a power control 360. The set of I/O connections 355 may be positioned about the exterior of power source 350 and may include, for example, one or more power connectors, universal serial bus connectors, or other connectors capable of receiving data, power, or both. Power control 360 can be any button, switch, paddle, dial, scroll wheel, or other input control that activates power source 350 when engaged by a user. Power source 350 can be battery powered or powered through a direct electrical connection with a conventional wall socket.

Dongle 400 communicates with the components of surgical control system 300 to allow for dual control of surgical stapling device 100 from control interface 500 and/or directly from stapling device 100. Dongle 400 comprises a microcontroller 402, or similar computing device, having a processing unit and a memory that may be configured with instructions to control dongle 400 and/or various other components, features, or aspects of surgical control system 300. Dongle 400 further comprises a set of I/O connections 404, a power control 406, and one or more light emitting diodes (LEDs) 408 indicating power of dongle 400. The set of I/O connections 404 may be positioned about the exterior of dongle 400 and may include, for example, one or more power connectors or receivers, universal serial bus connectors, or other connectors or cords capable of receiving data, power, or both. An override control 410 may be positioned on dongle 400 to disable control of stapling device 100 bedside, should the doctor want full control of stapling device 100. Communication device 412 may be one or more of a Bluetooth transceiver, Wi-Fi transceiver, cellular data transceiver, IBEACONS, near field communications, Ethernet, or other wireless or wired communication device capable of exchanging information and data between dongle 400 and surgical stapling device 100, while also allowing for communication between dongle 400 and other components such as control interface 500. Power control 406 and override control 410 can be any button, switch, paddle, dial, scroll wheel, or other input control.

Control interface 500 may be any manually controlled device, such as a foot-operated device, a hand-operated device, voice recognition device, or any other suitable device, that is communicatively coupled to dongle 400 and surgical stapling device 100. Control interface 500 includes a microcontroller 502, or similar computing device, having a processing unit and a memory that may be configured with instructions to control the control interface 500 and/or various other components, features, or aspects of surgical control system 300. Control interface 500 further comprises a power control 504 that functions to turn control interface 500 ON/OFF, one or more light emitting diodes (LEDs) 506 indicating power of control interface 500, and an override control 508 to disable control of stapling device 100 bedside, should the doctor want full control of stapling device 100. Communication device 510 may be one or more of a Bluetooth transceiver, Wi-Fi transceiver, cellular data transceiver, IBEACONS, near field communications, Ethernet, or other wireless or wired communication device capable of exchanging information and data between control interface 500 and surgical stapling device 100, while also allowing for communication between control interface 500 and other components such as dongle 400. Power control 504 and override control 508 can be any button, switch, paddle, dial, scroll wheel, or other input control.

Figure 5:
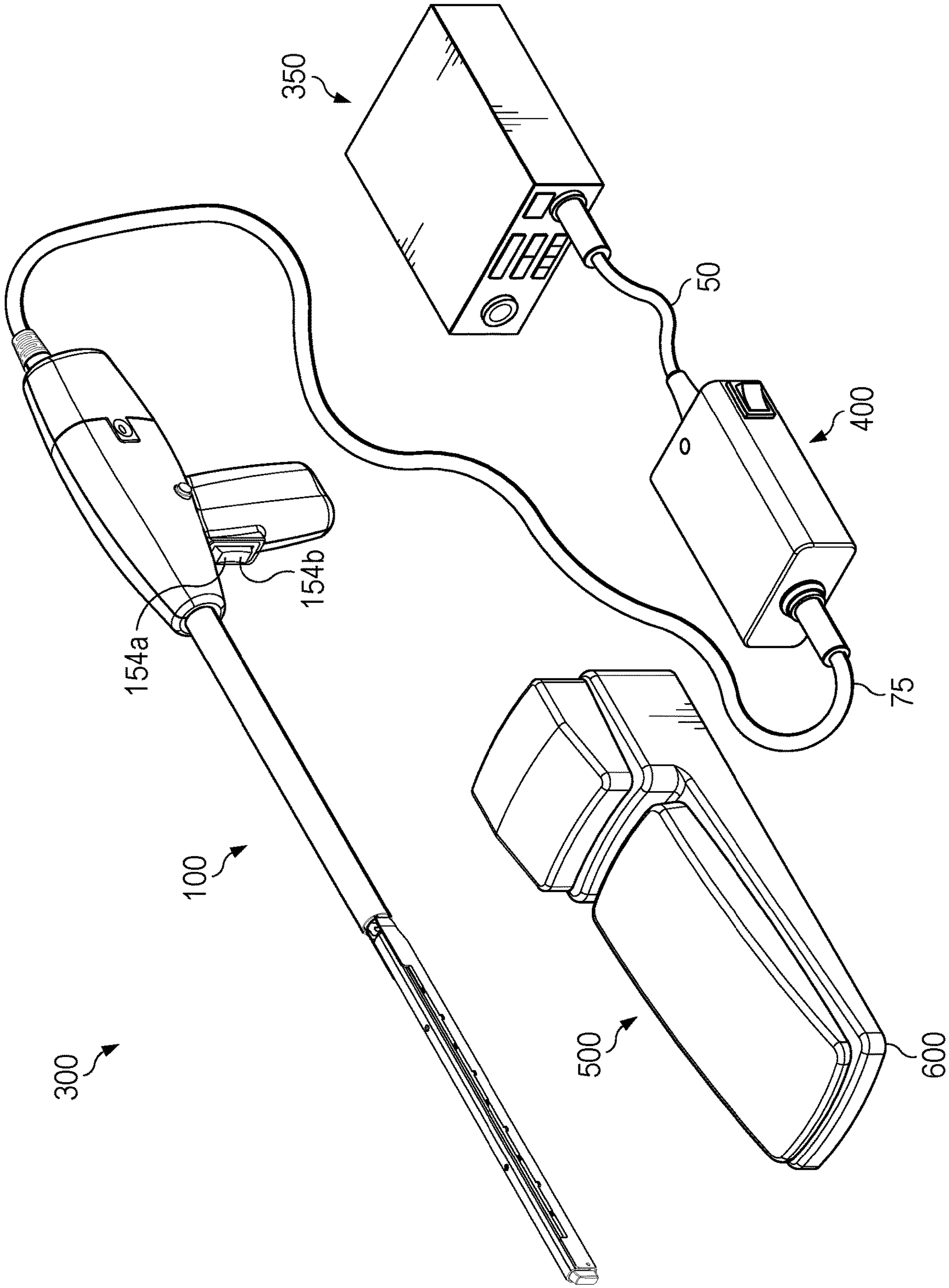
FIG. 5 depicts an exemplary configuration of the surgical control system of FIG. 4, wherein the control interface is a first exemplary foot pedal.
Figure 6:
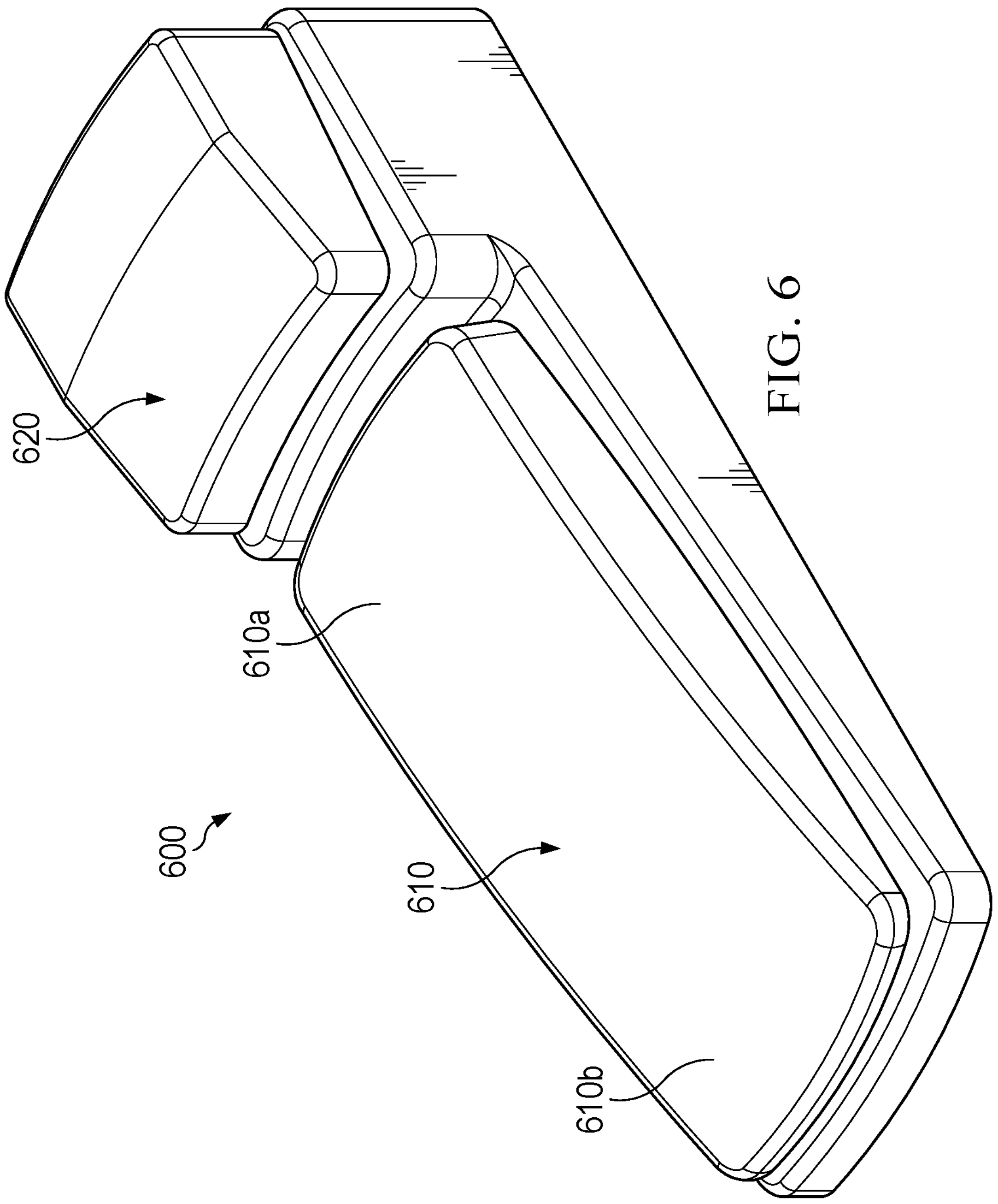
FIG. 6 is a perspective view of the foot pedal of FIG. 5.
Figure 7:
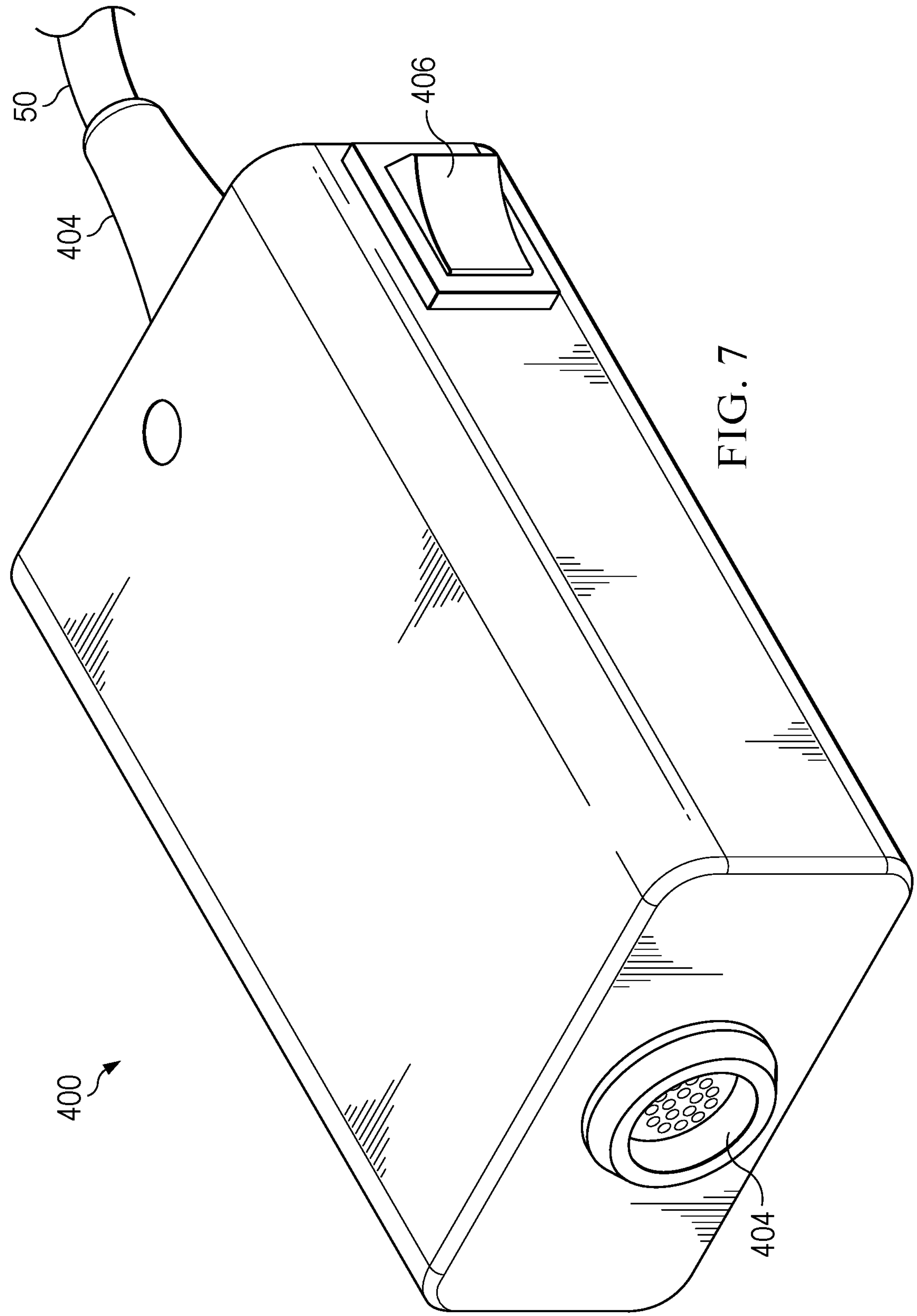
FIG. 7 is a perspective view of the dongle of FIG. 5.

FIG. 5 depicts an exemplary configuration of surgical control system 300 having surgical stapling device 100, power source 350, dongle 400, and control interface 500, wherein control interface 500 is a first exemplary foot pedal 600; FIG. 6 is a perspective view of foot pedal 600; and FIG. 7 is a perspective view of dongle 400. With reference to FIGS. 4-7, the use of dongle 400 creates a dual circuit allowing for control of surgical stapling device 100 from foot pedal 600 and/or directly from stapling device 100. In the present exemplary embodiment, dongle 400 is coupled to power source 350 through power cord or similar attachment device 50, and stapling device 100 is coupled to dongle 400 via power cord or similar attachment device 75. Once stapling device 100 is coupled to dongle 400, and dongle 400 is coupled to power source 350, power controls 406, 504 can be engaged to turn ON dongle 400 and foot pedal 600, respectively, thereby pairing dongle 400 with both stapling device 100 and foot pedal 600.

Foot pedal 600, which functions as control interface 500 and which may be configured for use with surgeon's console 210 that is remote from stapling device 100, comprises a rocker switch 610 and a top button 620. Rocker switch 610 includes a top rocker switch 610*a* and a bottom rocker switch 610*b*, wherein top rocker switch 610*a* corresponds and coordinates with up switch 154*a* of trigger 154 on stapling device 100, and wherein bottom rocker switch 610*b* corresponds and coordinates with down switch 154*b* of trigger 154. Top button 620 corresponds and coordinates with mode button 156 to control operational modes and to function as a safety button/switch for operating the firing mechanism of surgical stapling device 100.

In one exemplary method or process, activating top rocker switch 610*a* opens the jaws (i.e. clamping mechanism) of surgical stapling device 100. Once opened, an organ or other tissue can be placed within the clamping mechanism of stapling device 100, and bottom rocker switch 610*b* is then activated to close the clamping mechanism on the organ or other tissue. Once stapling device 100 is fully closed, a first activation of top button 620 causes stapling device 100 to enter a firing mode and begin a 15 second timeout prior to surgical stapling device 100 fully entering firing mode. The timeout period provides the surgeon with a final opportunity to ensure no unintended objects or tissue are within the clamping mechanism prior to firing. If the system 300 determines the jaws of surgical stapling device 100 are not fully closed, stapling device 100 will not enter firing mode and activating top button 620 will cause no action. During the timeout period, any activation of rocker switch 610 will cancel the firing mode, and to re-enter firing mode, top button 620 will have to be re-activated. Once the 15 second timeout period has ended, a second activation of top button 620 causes stapling device 100 to fully enter the firing mode. Top rocker switch 610*a* or bottom rocker switch 610*b* can then be activated to deploy the staple line and simultaneously cut tissue.

Because stapling deice 100 is controllable from either foot pedal 600 or directly from stapling device 100, whichever is activated first (foot pedal 600 or stapling device 100) will have precedence over a later activated switch/button. For example, if up switch 154*a* of stapling device 100 activated bedside by the nurse or other operating room staff member prior to the surgeon activating, for example, top button 620, activation of up switch 154*a* will take precedence and cause the clamping mechanism to open instead of entering firing mode. However, as previously discussed, foot pedal 600 and/or dongle 400 may include override controls 410, 508, respectively, which, when activated, gives the surgeon operating foot pedal 600 total control over stapling device 100 such that the nurse or other operating room staff member holding stapling device 100 bedside will be unable to activate stapling device 100 in any manner.

Figure 8:
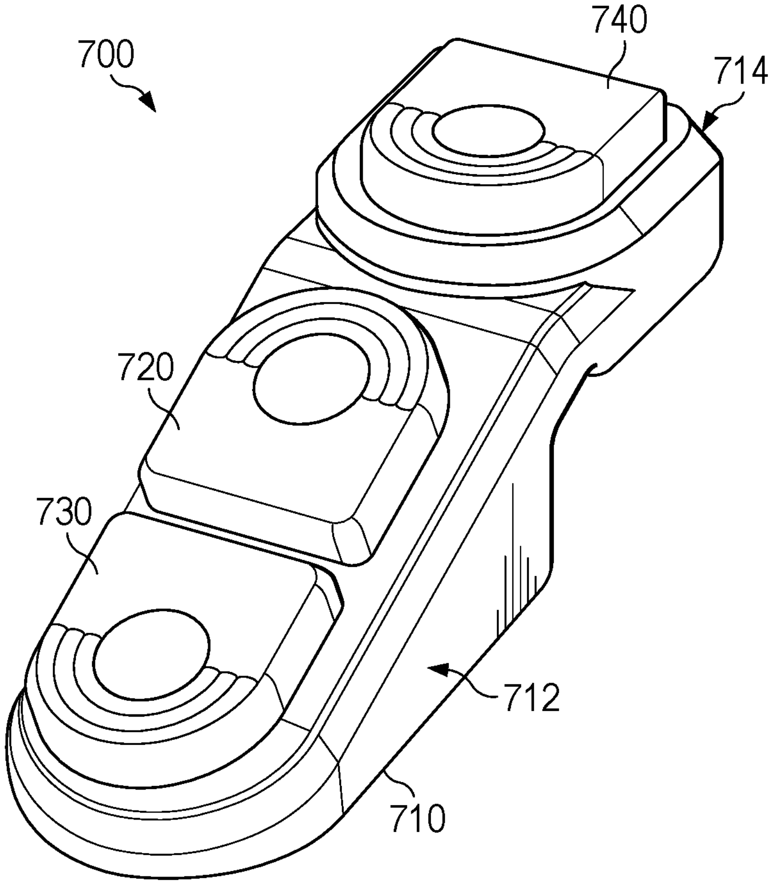
FIG. 8 depicts another exemplary control interface for use with the surgical control system of FIG. 4, wherein the control interface is another exemplary foot pedal.
Figure 9:
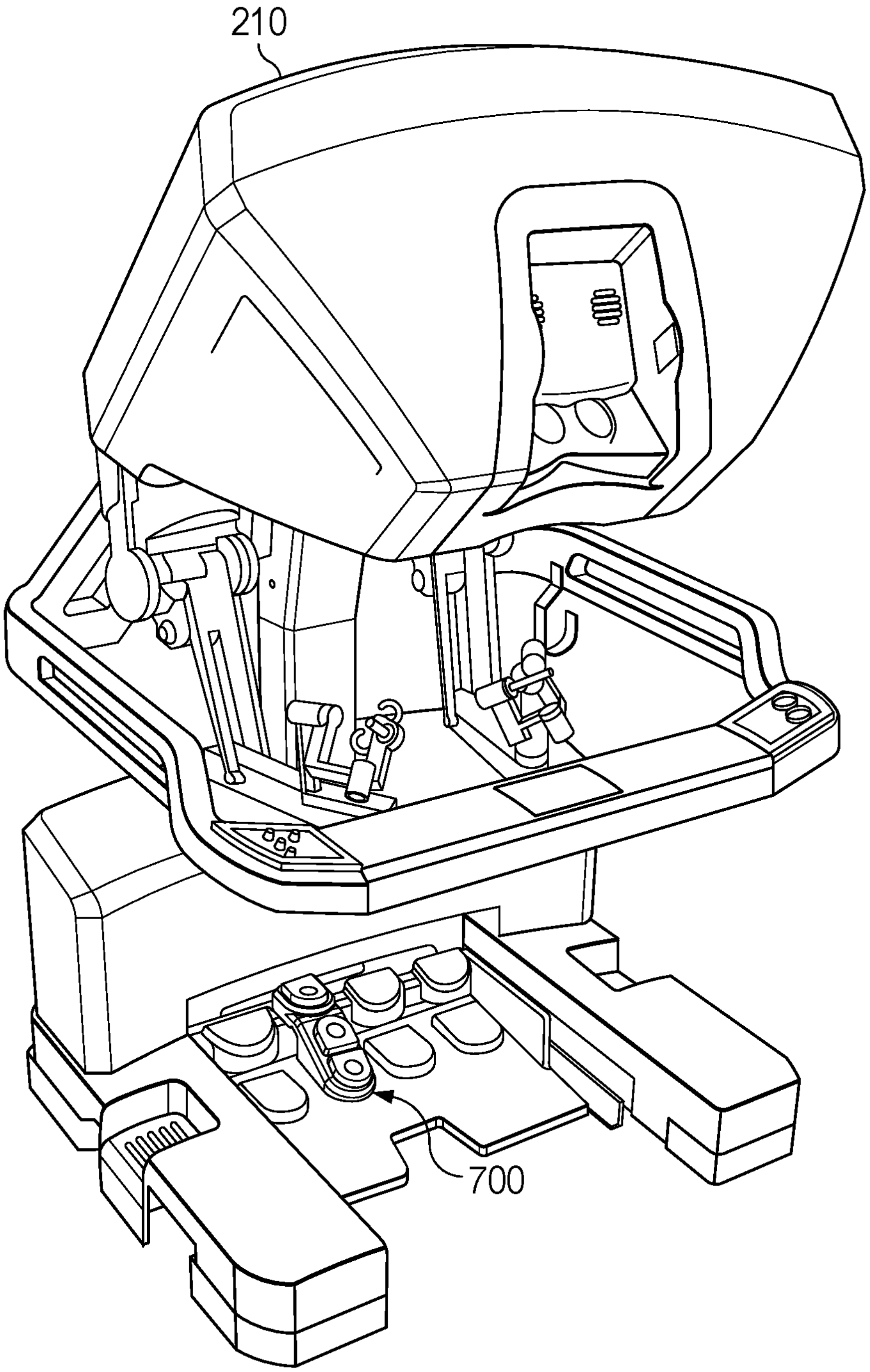
FIG. 9 depicts the control interface of FIG. 8 integrated with the surgical console of FIG. 3.

FIG. 8 depicts another exemplary foot pedal 700 that corresponds to control interface 500 and is configured for use with surgical control system 300; and FIG. 9 depicts foot pedal 700 incorporated into surgical console 210. With reference to FIGS. 8-9, foot pedal 700 functions similarly and includes similar components to that of foot pedal 600, the difference being that foot pedal 700 is more integrally configured into a foot panel area of surgical console 210. Foot pedal 700 includes a base 710 having a first portion 712 and a second portion 714, wherein first portion 712 is offset from second portion 714. A top switch 720 and a bottom switch 730 are disposed on first portion 712 of base 710, and a top button 740 is disposed on second portion 714 of base 710. Top switch 720 and bottom switch 730 correspond and coordinate with up switch 154*a* and down switch 154*b* of trigger 154, respectively, on stapling device 100. Top button 740 corresponds and coordinates with mode button 156 to control operational modes and to function as a safety button/switch for operating the firing mechanism of surgical stapling device 100. Similar to the previous foot pedals discussed herein, foot pedal 700 can include override control 508 to provide the surgeon operating foot pedal 700 total control over stapling device 100.

In one exemplary method or process, activating top switch 720 opens the jaws (i.e. clamping mechanism) of surgical stapling device 100. Once opened, an organ or other tissue can be placed within the clamping mechanism of stapling device 100, and bottom switch 730 is then activated to close the clamping mechanism on the organ or other tissue. Once stapling device 100 is fully closed, a first activation of top button 740 causes stapling device 100 to enter a firing mode and begin a 15 second timeout period prior to surgical stapling device 100 fully entering firing mode. This timeout period provides the surgeon with a final opportunity to ensure no unintended objects or tissue are within the clamping mechanism prior to firing. If the system 300 determines the jaws of surgical stapling device 100 are not fully closed, stapling device 100 will not enter firing mode and activating top button 740 will cause no action. Once the 15 second timeout period has ended, a second activation of top button 740 causes stapling device 100 to fully enter the firing mode. Top switch 720 or bottom switch 730 can then be activated to deploy the staple line and simultaneously cut tissue. Because stapling deice 100 is controllable from either foot pedal 700 or directly from stapling device 100, whichever is activated first (foot pedal 700 or stapling device 100) will have precedence over a later activated switch/button.

Figure 10:
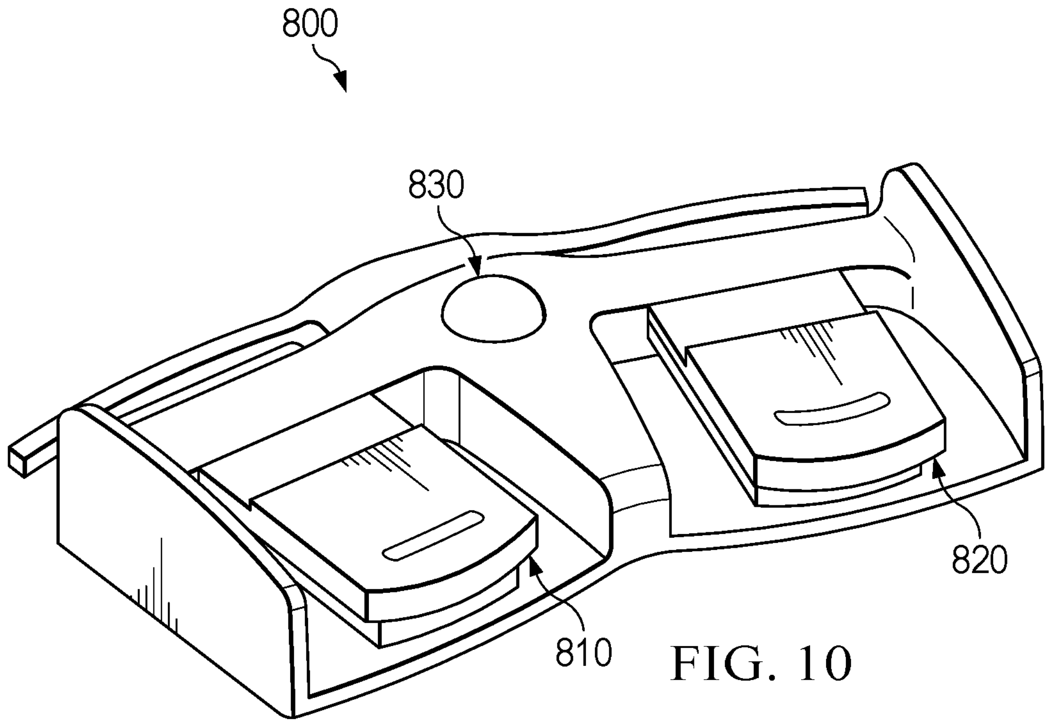
FIG. 10 depicts still another exemplary control interface for use with the surgical control system of FIG. 4, wherein the control interface is still another exemplary foot pedal.
Figure 11:
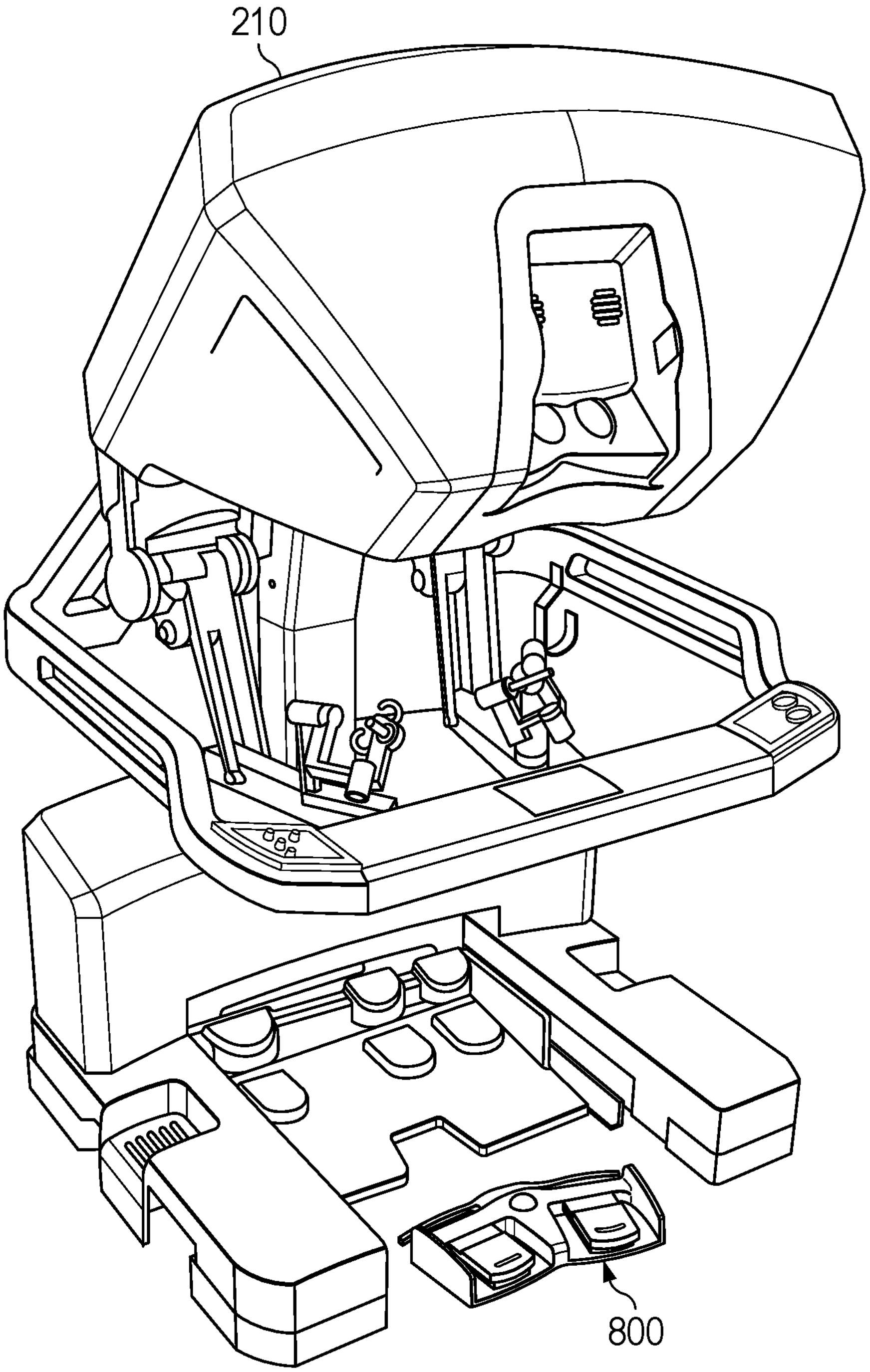
FIG. 11 depicts the control interface of FIG. 10 integrated with the surgical console of FIG. 3.

FIG. 10 depicts still another exemplary foot pedal 800 that corresponds to control interface 500 and that is configured for use with a foot panel area of surgical control system 300; and FIG. 11 depicts foot pedal 800 incorporated into surgical console 210. With reference to FIGS. 10-11, foot pedal 800 functions similarly and includes similar components to that of foot pedals 600 and 700, the difference being that foot pedal 800 is configured to include a left switch 810, a right switch 820, and a top button 830. Left switch 810 and right switch 820 correspond and coordinate with up switch 154*a* and down switch 154*b* of trigger 154, respectively, on stapling device 100. In this embodiment, right switch 820 is also configured to fire the stapling device 100. Top button 830 corresponds and coordinates with mode button 156 to control operational modes and to function as a safety button/switch for operating the firing mechanism of surgical stapling device 100. Similar to the previous foot pedals discussed herein, foot pedal 800 can include override control 508 to provide the surgeon operating foot pedal 800 total control over stapling device 100.

In one exemplary method or process, activating left switch 810 opens the jaws (i.e. clamping mechanism) of surgical stapling device 100. Once opened, an organ or other tissue can be placed within the clamping mechanism of stapling device 100, and right switch 820 is then activated to close the clamping mechanism on the organ or other tissue. Once stapling device 100 is fully closed, top button 830 is activated to cause stapling device 100 to enter a firing mode and begin a 15 second timeout prior to surgical stapling device 100 fully entering firing mode. This timeout period provides the surgeon with a final opportunity to ensure no unintended objects or tissue are within the clamping mechanism prior to firing. If the system 300 determines the jaws of surgical stapling device 100 are not fully closed, stapling device 100 will not enter firing mode and activating top button 830 will cause no action. During the timeout period, any activation of either left switch 810 or right switch 820 will cancel the firing mode, and to re-enter firing mode, top button 830 will have to be re-activated. Once the 15 second timeout period has ended, a second activation of top button 830 causes stapling device 100 to fully enter the firing mode. Left switch 810 or right switch 820 can then be activated to deploy the staple line and simultaneously cut tissue. Because stapling deice 100 is controllable from either foot pedal 800 or directly from stapling device 100, whichever is activated first (foot pedal 800 or stapling device 100) will have precedence over a later activated switch/button.

Figure 12A:
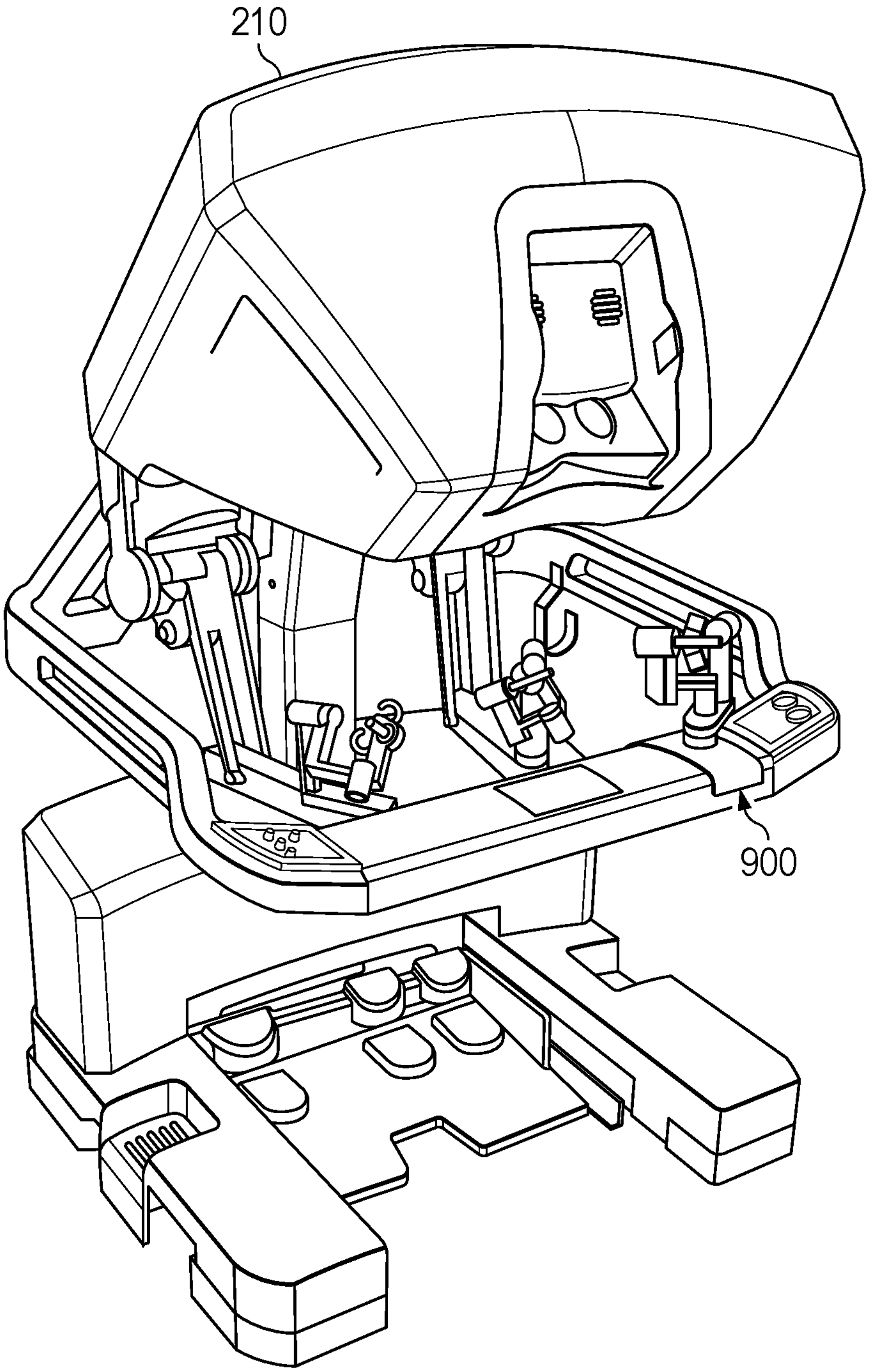
Figure 12B:
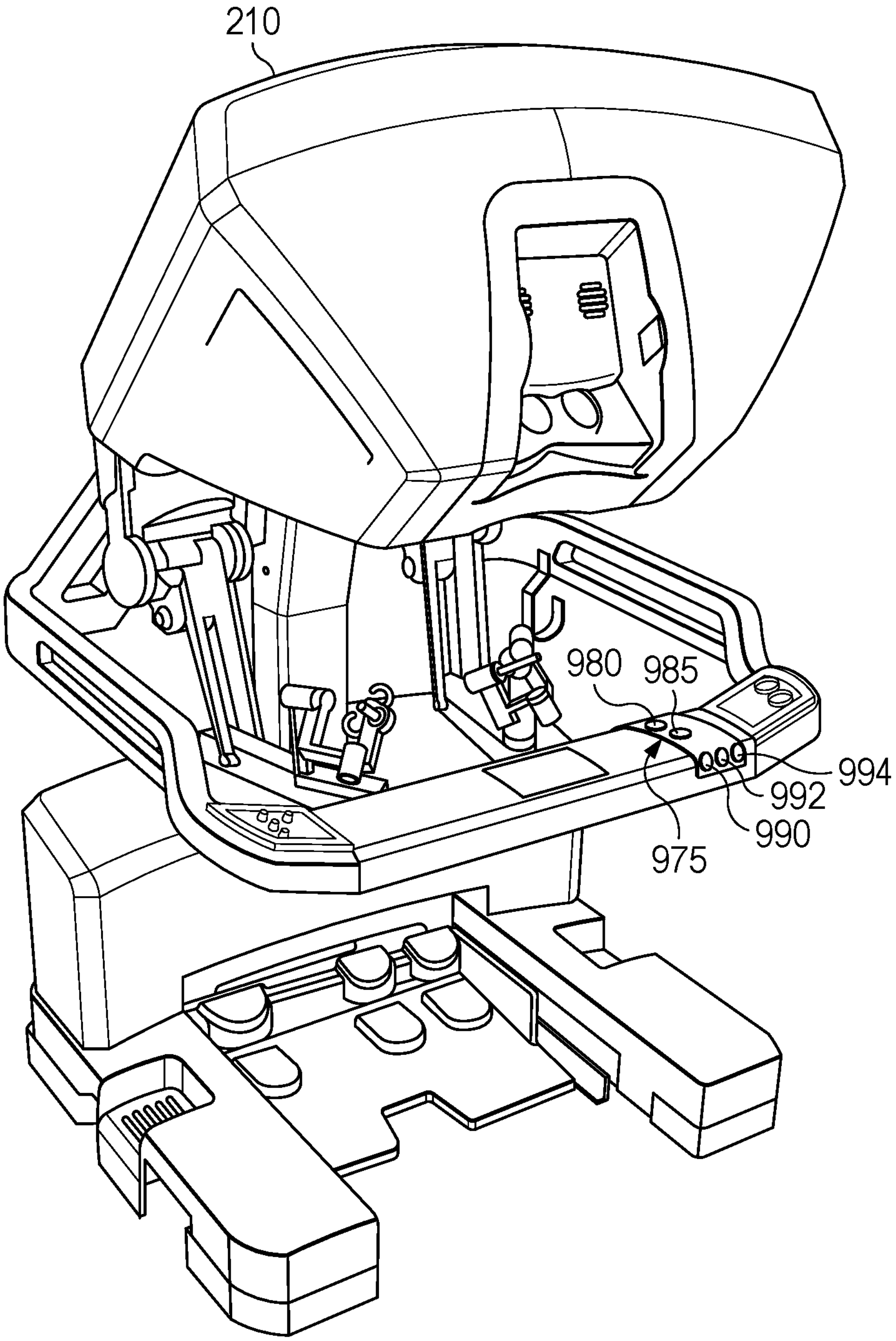
Figure 13:
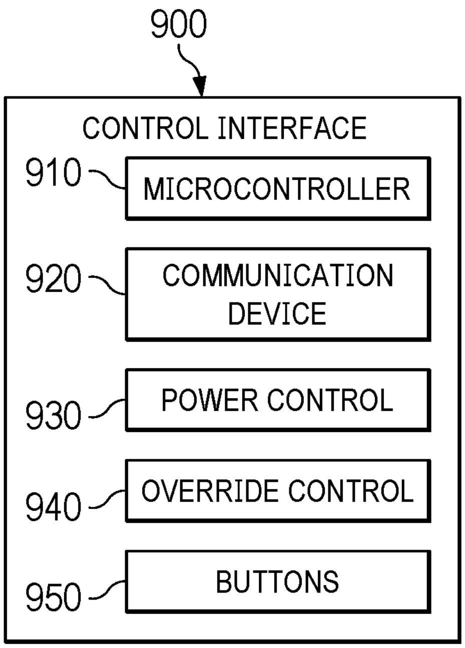
FIG. 13 is a block diagram of the hand control of FIG. 12A showing its basic components.

FIGS. 12A-12B depict additional exemplary hand-operable control interfaces configured for use with surgical control system 300, wherein FIG. 12A depicts the control interface as a hand control 900; and wherein FIG. 12B depicts the control interface as a hand-operated control panel 975. FIG. 13 is a block diagram of hand control 900 showing its basic components. When implemented into surgical control system 300 as a control interface, hand control 900 and hand-operated control panel 975 both function similarly to that of foot pedals 600, 700, 800, the difference being that doctors and qualified individuals can control surgical stapler 100 at a remote location at surgical console 210 with their hands and fingers, rather than their feet. Hand control 900 and hand-operated control panel 975 are each positionable at any location, and/or slidable, about the exterior of surgical console 210.

With reference to FIGS. 12A and 13, hand control 900, which may be a manual controller or other motion control device having one or more degrees of freedom, includes a microcontroller 910, or similar computing device, having a processing unit and a memory that may be configured with instructions to control hand control 900 and/or various other components, features, or aspects of surgical control system 300. Hand control 900 further comprises a communication device 920, a power control 930 that functions to turn hand control 900 ON/OFF, and an override control 940 to disable control of stapling device 100 bedside, should the doctor want full control of stapling device 100. Communication device 920 may be one or more of a Bluetooth transceiver, Wi-Fi transceiver, cellular data transceiver, IBEACONS, near field communications, Ethernet, or other wireless or wired communication device capable of exchanging information and data between hand control 900 and surgical stapling device 100, while also allowing for communication between hand control 900 and other components such as dongle 400. Power control 930 and override control 940 can be any button, switch, paddle, dial, scroll wheel, or other input control.

One or more buttons or similar input controls 950 may be positioned about the exterior of hand control 900 to correspond and coordinate with trigger 154 of surgical stapling device 100. Similar to that of the other control interfaces disclosed herein, one or more buttons 950 can open and close the jaws (i.e. clamping mechanism) of surgical stapling device 100, control operational modes and function as a safety button, and/or fire the stapling device 100. Further, physical manipulations of hand control 900 by the doctor or qualified individual may be converted into physical motions of arm 250 of mobile cart 240.

Now referring to FIG. 12B, hand-operated control panel 975 comprises a power control 980 that functions to turn control panel 975 ON/OFF, and an override control 985 to disable control of stapling device 100 bedside, should the doctor want full control of stapling device 100. Buttons 990, 992, 994, or similar input controls, are positioned about the exterior of control panel 975. Similar to that of the other control interfaces disclosed herein, buttons 990, 992, 994 can open and close the jaws (i.e. clamping mechanism) of surgical stapling device 100, control operational modes and function as a safety button, and/or fire the stapling device 100. It is to be understood that control panel 975 includes a microcontroller (or similar computer device) and a communication device similar to that of microcontroller 910 and communication device 920 of hand control 900. Power control 980 and override control 985 can be any button, switch, paddle, dial, scroll wheel, or other input control. Placement of power control 980, override control 985, and buttons 990, 992, 994 on control panel 975 are non-limiting, and it is to be understood that control panel 975 can be any shape that reasonably corresponds to the exterior of surgical console 210, including but not limited to, square, rectangular, spherical, or triangular.

Figure 14:
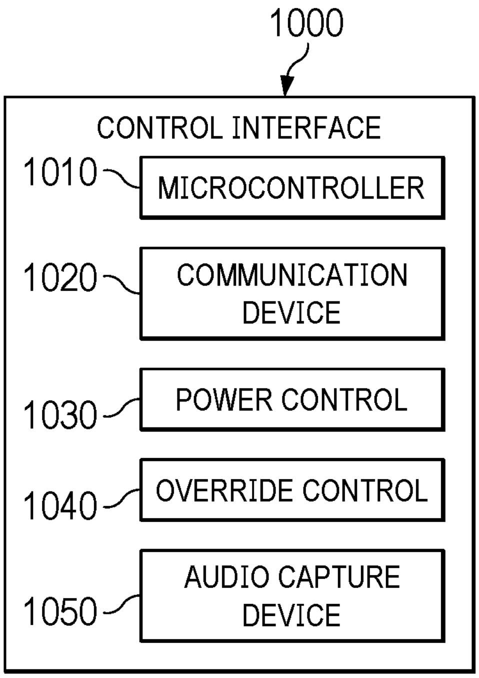
FIG. 14 is a block diagram of still another exemplary control interface for use with the surgical control system of FIG. 4, wherein the control interface is an audio recognition device.

FIG. 14 is a block diagram still another exemplary control interface configured for use with surgical control system 300, wherein the control interface is an audio recognition device 1000. When implemented into surgical control system 300, audio recognition device 1000 (e.g. a laptop or other computer with an integrated or attached audio capture device, mobile device such as a smart phone or tablet, or devices having features and capabilities similar to any of the above) functions similarly to that of the other control interfaces disclosed herein, the difference being that doctors and qualified individuals can control surgical stapler 100 at a remote location at surgical console 210 by voice or audio commands and instructions.

With reference to FIG. 14, audio recognition device 1000 includes a microcontroller 1010, or similar computing device, having a processing unit and a memory that may be configured with instructions to control recognition device 1000 and/or various other components, features, or aspects of surgical control system 300. Recognition device 1000 further comprises a communication device 1020, a power control 1030 that functions to turn recognition device 1000 ON/OFF, and an override control 1040 to disable control of stapling device 100 bedside, should the doctor want full control of stapling device 100 from surgical console 210. Communication device 1020 may be one or more of a Bluetooth transceiver, Wi-Fi transceiver, cellular data transceiver, IBEACONS, near field communications, Ethernet, or other wireless or wired communication device capable of exchanging information and data between audio recognition device 1000 and surgical stapling device 100, while also allowing for communication between audio recognition device 1000 and other components such as dongle 400. Power control 1030 and override control 1040 can be any button, switch, paddle, dial, scroll wheel, or other input control.

Audio recognition device 1000 includes one or more audio capture devices 1050, such as a microphone, that is capable of capturing audio, speech, or other data. Microcontroller 1010 stores and analyzes the audio received from capture devices 1050 to determine a meaning of the audio and instructs surgical stapler 100 and dongle 400, via communication device 1020, to perform specific commands based on the meaning of the audio. The processor of microcontroller 1010 may be configured to analyze the audio received from capture devices 1050 through one or more language analysis functions and models, such as, for example, artificial intelligence or other machine learning modules. For example, specific voice commands/instructions transmitted via communication device 1020 can correspond to the opening and closing of the jaws (i.e. clamping mechanism) of surgical stapling device 100, initiating one or more safety features, and/or firing the stapling device 100.

The disclosed surgical control systems comprise a surgical stapling device coupled to a dongle via a power cord or similar attachment device; however, it is to be understood that surgical stapling device can be a non-corded, battery powered device that wirelessly communicates with the dongle and/or the one or more of the disclosed control interfaces (i.e. foot pedals, hand control, hand-operated control panel, and/or audio recognition device). The dongles used with the disclosed surgical control systems are separate components that are electrically and communicatively connected between the surgical stapling device and the power source; however, it is to be understood that the dongle could be incorporated into the surgical stapling device or the power source itself to reduce the size of the systems while maintain allow dual control of the stapling device from one or more of the disclosed control interfaces and/or directly from the surgical stapler.

The terms switches, buttons, and pedals used in conjunction with the disclosed surgical control systems are not so limited and can be any input control that functions similarly, such as, for example, buttons, switches, paddles, dials, scroll wheels, or the like.

The timeout period used with the disclosed surgical control systems can a period longer or shorter than 15 seconds, and the timeout period can be accompanied by a visual alert (e.g. flashing light or other visible indicators) and/or an audible alert (e.g. audio component or other audio indicators, such as a machine simulated voice or sound), which indicates the start and end of the timeout period and/or the remaining time left.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differ from or contradict this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about", if or when used throughout this specification describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed technology. Various functions and elements described herein may be partitioned differently from those shown without departing from the scope of the disclosed technology. Generic principles defined herein may be applied to other implementations. Different numbers of a given module or unit may be employed, a different type or types of a given module or unit may be employed, a given module or unit may be added, or a given module or unit may be omitted.

Regarding this disclosure, the term "a plurality of" refers to two or more than two. Unless otherwise clearly defined, orientation or positional relations indicated by terms such as "upper" and "lower" are based on the orientation or positional relations as shown in the figures, only for facilitating description of the disclosed technology and simplifying the description, rather than indicating or implying that the referred devices or elements must be in a particular orientation or constructed or operated in the particular orientation, and therefore they should not be construed as limiting the disclosed technology. The terms "connected", "mounted", "fixed", etc. should be understood in a broad sense. For example, "connected" may be a fixed connection, a detachable connection, or an integral connection; a direct connection, or an indirect connection through an intermediate medium. For an ordinary skilled in the art, the specific meaning of the above terms in the disclosed technology may be understood according to specific circumstances.

Specific details are given in the above description to provide a thorough understanding of the disclosed technology. However, it is understood that the disclosed embodiments and implementations can be practiced without these specific details. For example, circuits can be shown in block diagrams in order not to obscure the disclosed implementations in unnecessary detail. In other instances, well-known circuits, processes, algorithms, structures, and techniques can be shown without unnecessary detail in order to avoid obscuring the disclosed implementations.

Implementation of the techniques, blocks, steps and means described above can be accomplished in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

The disclosed technology can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, the disclosed technology can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

It should be appreciated that all combinations of the foregoing concepts and additional concepts discussed in greater detail herein (provided such concepts are not mutually inconsistent) are contemplated as being part of the disclosed technology. In particular, all combinations of claimed subject matter appearing at the end of this disclosure are contemplated as being part of the technology disclosed herein. While the disclosed technology has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed technology in its broader aspects is not limited to any of the specific details, representative devices and methods, and/or illustrative examples shown and described. Accordingly, departures may be made from such details without departing from the spirit or scope of the general inventive concept.

What is claimed:

1. A surgical control system for use with a computerized surgical manipulation system, comprising:

(a) a control interface communicatively coupled to a laparoscopic device detached from a robot of a computerized surgical manipulation system, wherein the control interface is positioned at a location physically remote from the laparoscopic device; and (b) a dongle communicatively coupled to the control interface and the laparoscopic device, wherein the dongle is configured to enable operation of the laparoscopic device from the control interface and directly from the laparoscopic device, and wherein the dongle allows for dual control of the laparoscopic device such that the laparoscopic device is controllable either from the control interface and/or directly from the laparoscopic device.

2. The surgical control system of claim 1, wherein the control interface or the dongle includes an override feature that, when activated, disables direct operation from the laparoscopic device, but maintains operation of the laparoscopic device from the control interface.

3. The surgical control system of claim 1, wherein the laparoscopic device is a surgical stapler configured to staple an anatomical structure of a patient during a minimally invasive procedure, the surgical stapler comprising:

(a) an end effector having a clamping mechanism with an anvil assembly and a cartridge assembly; and (b) an operating system comprising a trigger having an up-switch and a down-switch, wherein activation of the up-switch opens the clamping mechanism, and wherein activation of the down-switch closes the clamping mechanism.

4. The surgical control system of claim 3, wherein the control interface is a foot-operable device comprising a plurality of input controls, wherein each of the input controls, when activated, communicate with the operating system of the surgical stapler to perform an action.

5. The surgical control system of claim 4, wherein:

(a) activation of a first input control opens the clamping mechanism of the end effector;

(b) activation of a second input control closes the clamping mechanism of the end effector;

(c) first activation of a third input control initiates a timeout period before the surgical stapler cuts and staples the anatomical structure of the patient; and (d) second activation of the third input control causes the surgical stapler to enter a firing mode.

6. The surgical control system of claim 5, wherein the timeout period includes an alert configured to indicate a start of the timeout period, an end of the timeout period, remaining time of the timeout period, or combinations thereof, wherein the alert is a visual indicator, an audio indicator, or combinations thereof.

7. The surgical control system of claim 5, wherein the timeout period lasts 15 second.

8. The surgical control system of claim 4, wherein the plurality of input controls include buttons, switches, pedals, or combination thereof.

9. The surgical control system of claim 4, wherein the foot-operable device is integrated into a surgical console of the computerized surgical manipulation system.

10. The surgical control system of claim 3, wherein the control interface is a hand-operable device positioned on an exterior of a surgeon console of the computerized surgical manipulation system, the hand-operable device comprising a plurality of input controls, wherein each of the input controls, when activated, communicate with the operating system of the surgical stapler to perform an action.

11. The surgical control system of claim 10, wherein the plurality of input controls include buttons or switches which, when activated, open the clamping mechanism, close the clamping mechanism, enter a firing mode, or combinations thereof.

12. The surgical control system of claim 10, wherein the hand-operable device is a hand control that moves with one or more degrees of freedom, or a control panel.

13. The surgical control system of claim 3, wherein the control interface is an audio recognition device having a microcontroller configured to:

(a) receive audio content from an audio capture device during the minimally invasive procedure, wherein the audio content is one or more instructions from a user;

(b) analyze the audio content to determine a meaning for the one or more instructions; and (c) provide a command to the surgical stapler to perform one or more actions based on the meaning of the one or more instructions.

14. The surgical control system of claim 13, wherein the one or more actions include opening the clamping mechanism, closing the clamping mechanism, enter a firing mode, or combinations thereof.

15. The surgical control system of claim 1, wherein the detached laparoscopic device is supported by a trained individual positioned bedside to a patient.

16. The surgical control system of claim 1, wherein the dongle is incorporated into the laparoscopic device.

17. A surgical control system for use with a computerized surgical manipulation system, comprising:

(a) a surgical stapler configured to staple an anatomical structure of a patient during a minimally invasive procedure, the surgical stapler including:

(i) an end effector having a clamping mechanism with an anvil assembly and a cartridge assembly; and (ii) an operating system comprising a trigger having an up-switch and a down-switch, and wherein activating the up-switch opens the clamping mechanism, wherein activating the down-switch closes the clamping mechanism;

(b) a control interface communicatively coupled to the surgical stapler, wherein the control interface is positioned at the computerized surgical manipulation system physically remote from the surgical stapler; and (c) a dongle communicatively coupled to the control interface and the surgical stapler, wherein a microcontroller of the dongle is configured to enable operation of the surgical stapler from the control interface and directly from the surgical stapler, wherein the dongle allows for dual control of the surgical stapler such that the surgical stapler is controllable either from the control interface and/or directly from the surgical stapler, wherein the control interface or the dongle includes an override feature that, when activated, disables direct operation from the surgical device, but maintains operation of the surgical device from the control interface, and wherein the surgical stapler is separate from the computerized surgical manipulation system and supported by a trained individual positioned bedside to the patient.

18. The surgical control system of claim 17, wherein the control interface is a foot-operable device comprising a plurality of input controls, wherein each of the input controls, when activated, communicate with the operating system of the surgical stapler to perform an action.

19. The surgical control system of claim 17, wherein the control interface is a hand-operable device positioned on an exterior of a surgeon console of the computerized surgical manipulation system, the hand-operable device comprising a plurality of input controls, wherein each of the input controls, when activated, communicate with the operating system of the surgical stapler to perform an action.

20. The surgical control system of claim 17, wherein the control interface is an audio recognition device having a microcontroller configured to:

(a) receive audio content from an audio capture device during the minimally invasive procedure, wherein the audio content is one or more instructions from a user;

(b) analyze the audio content to determine a meaning for the one or more instructions; and (c) provide a command to the surgical stapler to perform one or more actions based on the meaning of the one or more instructions.

* * * * *